(12) United States Patent
Smith

(10) Patent No.: US 8,454,590 B2
(45) Date of Patent: Jun. 4, 2013

(54) ENHANCED LOSSLESS CURRENT SENSE CIRCUIT

(75) Inventor: Robert B. Smith, Loveland, CO (US)

(73) Assignee: Covidien LP, Mansfield, MA (US)

( * ) Notice: Subject to any disclaimer, the term of this patent is extended or adjusted under 35 U.S.C. 154(b) by 548 days.

(21) Appl. No.: 12/713,956

(22) Filed: Feb. 26, 2010

(65) Prior Publication Data

US 2011/0213354 A1   Sep. 1, 2011

(51) Int. Cl.
A61B 18/14 (2006.01)

(52) U.S. Cl.
USPC .......................................... 606/34; 323/290

(58) Field of Classification Search
USPC ..... 606/32–35; 323/282, 284, 290; 324/76.11
See application file for complete search history.

(56) References Cited

U.S. PATENT DOCUMENTS

| | | | |
|---|---|---|---|
| 5,414,238 A | 5/1995 | Steigerwald et al. | |
| 6,469,481 B1 * | 10/2002 | Tateishi | 323/282 |
| 6,646,450 B2 * | 11/2003 | Liebler | 324/630 |
| 7,244,255 B2 | 7/2007 | Daners et al. | |
| D574,323 S | 8/2008 | Waaler | |
| 7,511,472 B1 | 3/2009 | Xia et al. | |
| 7,815,528 B2 | 10/2010 | Sullivan | |
| 7,956,620 B2 | 6/2011 | Gilbert | |
| 8,072,200 B1 * | 12/2011 | Qiu et al. | 323/282 |
| 8,152,802 B2 | 4/2012 | Podhajsky | |
| 8,162,932 B2 | 4/2012 | Podhajsky | |
| 8,167,875 B2 | 5/2012 | Podhajsky | |
| 8,211,100 B2 | 7/2012 | Podhajsky | |
| 8,231,553 B2 | 7/2012 | Joseph | |
| 8,262,652 B2 | 9/2012 | Podhajsky | |
| 2008/0203997 A1 | 8/2008 | Foran et al. | |
| 2009/0146635 A1 | 6/2009 | Qiu et al. | |
| 2010/0179533 A1 | 7/2010 | Podhajsky | |
| 2010/0191233 A1 | 7/2010 | Wham et al. | |
| 2010/0211063 A1 | 8/2010 | Wham | |
| 2010/0217258 A1 | 8/2010 | Floume | |
| 2010/0217264 A1 | 8/2010 | Odom | |
| 2011/0028963 A1 | 2/2011 | Gilbert | |
| 2011/0054460 A1 | 3/2011 | Gilbert | |
| 2011/0060329 A1 | 3/2011 | Gilbert | |
| 2011/0071516 A1 | 3/2011 | Gregg | |
| 2011/0071521 A1 | 3/2011 | Gilbert | |
| 2011/0077631 A1 | 3/2011 | Keller | |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

European Search Report for European Application No: 11155960 dated Jun. 10, 2011.

(Continued)

*Primary Examiner* — Michael Peffley

(57) ABSTRACT

A switched inductor system is provided that includes a switching regulator configured to receive an input signal and provide a voltage output, the switching regulator having one or more switches and one or more inductors. The system also includes a sensing circuit in parallel with the inductor. The sensing circuit includes a first RC circuit configured to detect an alternating current component of the voltage output and a second RC circuit configured to detect a direct current component of the voltage output.

9 Claims, 2 Drawing Sheets

U.S. PATENT DOCUMENTS

| | | |
|---|---|---|
| 2011/0112530 A1 | 5/2011 | Keller |
| 2011/0115562 A1 | 5/2011 | Gilbert |
| 2011/0144635 A1 | 6/2011 | Harper |
| 2011/0208179 A1 | 8/2011 | Prakash |
| 2011/0213354 A1 | 9/2011 | Smith |
| 2011/0213355 A1 | 9/2011 | Behnke, II |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 573301 | 5/1986 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |

OTHER PUBLICATIONS

Wald et al., "Accidental Burns", JAMA, Aug. 16, 1971, vol. 217, No. 7, pp. 916-921.

Vallfors et al., "Automatically Controlled Bipolar Electrosoagulation—'COA-COMP'" Neurosurgical Review 7:2-3 (1984) pp. 187-190.

Sugita et al., "Bipolar Coagulator with Automatic Thermocontrol" J. Neurosurg., vol. 41, Dec. 1944, pp. 777-779.

Muller et al. "Extended Left Hemicolectomy Using the LigaSure Vessel Sealing System" Innovations That Work; Company Newsletter; Sep. 1999.

Ogden Goertzel Alternative to the Fourier Transform: Jun. 1993 pp. 485-487 Electronics World; Reed Business Publishing, Sutton, Surrey, BG vol. 99, No. 9. 1687.

Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator" 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Geddes et al., "The Measurement of Physiologic Events by Electrical Impedence" Am. J. MI, Jan. Mar. 1964, pp. 16-27.

Cosman et al., "Methods of Making Nervous System Lesions" In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight And Absorbance Imaging Of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance" Applied Neurophysiology 51: (1988) pp. 230-242.

Ni W. et al. "A Signal Processing Method for the Coriolis Mass Flowmeter Based on a Normalized . . . " Journal of Applied Sciences—Yingyong Kexue Xuebao, Shangha CN, vo123 No. 2;(Mar. 2005); pp. 160-164.

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300" 1 p. Sep. 1998.

Valleylab Brochure "Valleylab Electroshield Monitoring System" 2 pp. Nov. 1995.

International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.

International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09012386 dated Apr. 1, 2010.
International Search Report EP09012392 dated Mar. 30, 2010.
International Search Report EP09012396 dated Apr. 7, 2010.
International Search Report EP09012400 dated Apr. 7, 2010.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10150564.2 dated Mar. 29, 2010.
International Search Report EP10150565.9 dated Mar. 12, 2010.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

* cited by examiner

ENHANCED LOSSLESS CURRENT SENSE CIRCUIT

BACKGROUND

1. Technical Field

The present disclosure relates generally to electrosurgical systems that utilize energy to perform electrosurgical procedures. More particularly, the present disclosure is directed to a switching power supply for an electrosurgical generator having a lossless current sense circuit.

2. Description of the Related Art

Electrosurgical generators are employed by surgeons in conjunction with an electrosurgical instrument to cut, coagulate, desiccate and/or seal patient tissue. High frequency electrical energy, e.g., radio frequency (RE) energy, is produced by the electrosurgical generator and applied to the tissue by the electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing possible damage to adjacent tissue, e.g., thermal spread, it is necessary to control the output from the electrosurgical generator, e.g., power, waveform, voltage, current, pulse rate, etc.

Energy is supplied to the electrode(s) by an electrosurgical generator coupled thereto. The electrosurgical generator may include a switched inductor system to provide an RF output to the electrode(s). Switched inductor systems utilize at least one switch, at least one diode and at least one inductor. As better low loss inductor elements are produced, it gets harder to measure the current through the inductor without considerable additional circuitry. The additional circuitry adds components, size and power consumption to a final product thereby negating the benefit of having a lossless detection method.

SUMMARY

The present disclosure relates to a switched inductor system that includes a switching regulator configured to receive an input signal and provide a voltage output, the switching regulator having one or more switches and one or more inductors. The system also includes a sensing circuit in parallel with the inductor having a first RC circuit configured to detect an alternating current component of the voltage output and a second RC circuit configured to detect a direct current component of the voltage output.

In one embodiment, the one or more switches may be a field effect transistor. Moreover, the first and second RC circuits may each include one or more resistors and one or more capacitors.

In another embodiment of the present disclosure, an electrosurgical generator is provided. The generator includes a controller configured to control a voltage output of the electrosurgical generator and a radio frequency output stage configure to output energy. The radio frequency output stage includes a switching regulator configured to receive an input signal from the controller and provide a voltage output, the switching regulator having one or more switches and one or more inductors. The radio frequency output stage also includes a sensing circuit in parallel with the inductor, the sensing circuit including a first RC circuit configured to detect an alternating current component of the voltage output and a second RC circuit configured to detect a direct current component of the voltage output. The sensing circuit provides the alternating current component and the direct current component of the voltage output to the controller and the controller controls the output of the electrosurgical generator based on the alternating current component and the direct current component of the voltage output.

The sensing circuit may further include an amplifier to amplify the direct current component of the voltage output. The one or more switches may be a field effect transistor. The first and second RC circuits may each include one or more resistors and one or more capacitors.

In yet another embodiment of the present disclosure, a lossless current sense circuit for detecting a voltage across an inductor is provided. The lossless current sense circuit includes a first RC circuit configured to detect an alternating current component of the voltage across the inductor, and a second RC circuit configured to detect a direct current component of the voltage across the inductor.

The lossless sense circuit may further include an amplifier to amplify the direct current component of the voltage output. The first and second RC circuits may each include one or more resistors and one or more capacitors.

BRIEF DESCRIPTION OF THE DRAWINGS

Various embodiments of the present disclosure are described herein with reference to the drawings wherein.

DETAILED DESCRIPTION

Figure 1A:
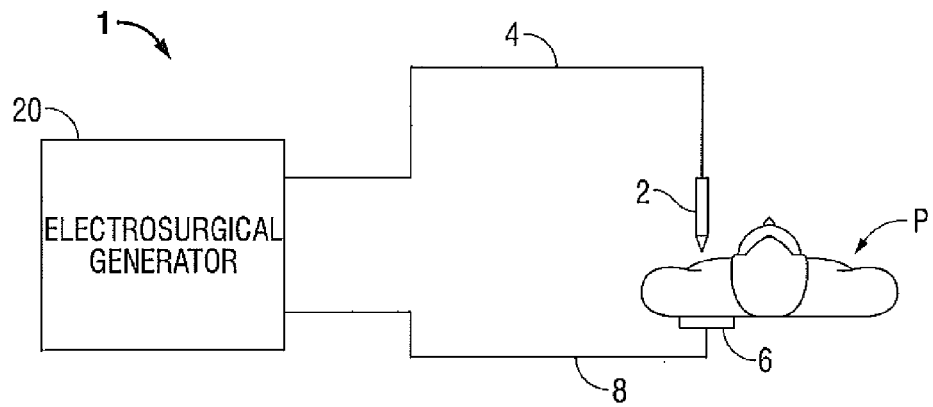
FIGS. 1A-1B are schematic diagrams of an electrosurgical system according to the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user. The term "clinician" refers to any medical professional (i.e., doctor, surgeon, nurse, or the like) performing a medical procedure involving the use of embodiments described herein.

As described in more detail below with reference to the accompanying figures, the present disclosure is directed to an enhanced lossless current sense apparatus for a switching power supply suitable for use in electrosurgical generators. The term "lossless" as used herein refers to a low loss circuit. The circuit utilized in the lossless current sense apparatus allows for simple high speed monitoring of cycle by cycle current in a switched inductor systems without high bandwidth precise active amplification thereby saving cost, space and power consumption.

A generator according to the present disclosure can perform monopolar and bipolar electrosurgical procedures, including tissue ablation procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

FIG. 1A is a schematic illustration of a monopolar electrosurgical system according to one embodiment of the present disclosure. The system includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via an supply line 4, which is connected to an active terminal 30 (FIG. 2) of the generator 20, allowing the instrument 2 to coagulate, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8 respectively.

The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

Figure 1B:
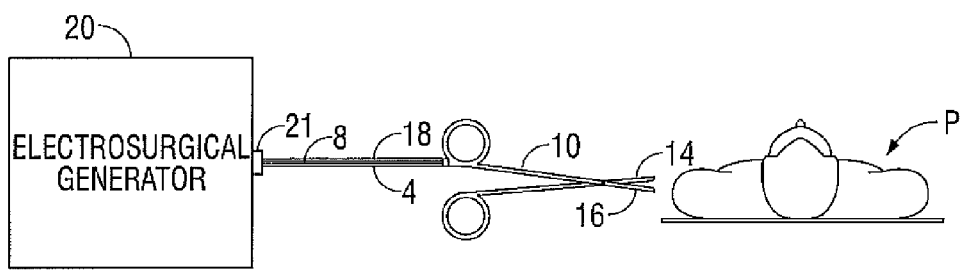
Figure 2:
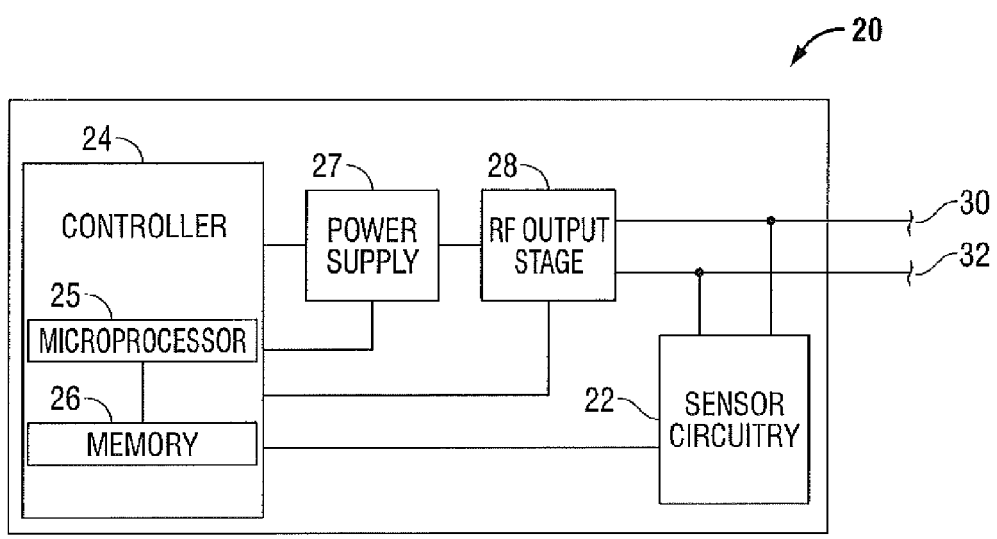
FIG. 2 is a schematic diagram of a generator control system according to an embodiment of the present disclosure.

FIG. 1B is a schematic illustration of a bipolar electrosurgical system according to the present disclosure. The system includes a bipolar electrosurgical forceps 10 having one or more electrodes for treating tissue of a patient P. The electrosurgical forceps 10 include opposing jaw members having an active electrode 14 and a return electrode 16 disposed therein. The active electrode 14 and the return electrode 16 are connected to the generator 20 through cable 18, which includes the supply and return lines 4, 8 coupled to the active and return terminals 30, 32, respectively (FIG. 2). The electrosurgical forceps 10 are coupled to the generator 20 at a connector 21 having connections to the active and return terminals 30 and 32 (e.g., pins) via a plug disposed at the end of the cable 18, wherein the plug includes contacts from the supply and return lines 4, 8.

Not explicitly shown in FIGS. 1A-B, the generator 20 includes suitable input controls (e.g., buttons, activators, switches, touch screen, etc.) for controlling the generator 20, as well as one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., tissue ablation). Further, the instrument 2 may include a plurality of input controls which may be redundant with certain input controls of the generator 20. Placing the input controls at the instrument 2 allows for easier and faster modification of RF energy parameters during the surgical procedure without requiring interaction with the generator 20.

FIG. 2 shows a schematic block diagram of the generator 20 having a controller 24, a power supply 27, an RF output stage 28, and a sensor module 22. The power supply 27 provides DC power to the RF output stage 28 which then converts the DC power into RF energy and delivers the RF energy to the instrument 2. The controller 24 includes a microprocessor 25 having a memory 26 which may be volatile type memory (e.g., RAM) and/or non-volatile type memory (e.g., flash media, disk media, etc.). The microprocessor 25 includes an output port connected to the power supply 27 and/or RE output stage 28 that allows the microprocessor 25 to control the output of the generator 20 according to either open and/or closed control loop schemes.

A closed loop control scheme generally includes a feedback control loop wherein the sensor module 22 provides feedback to the controller 24 (i.e., information obtained from one or more sensing mechanisms for sensing various tissue parameters such as tissue impedance, tissue temperature, output current and/or voltage, etc.). The controller 24 then signals the power supply 27 and/or RF output stage 28 which then adjusts the DC and/or RF power supply, respectively. The controller 24 also receives input signals from the input controls of the generator 20 and/or instrument 2. The controller 24 utilizes the input signals to adjust the power output of the generator 20 and/or instructs the generator 20 to perform other control functions.

The microprocessor 25 is capable of executing software instructions for processing data received by the sensor module 22, and for outputting control signals to the generator 20, accordingly. The software instructions, which are executable by the controller 24, are stored in the memory 26 of the controller 24.

The controller 24 may include analog and/or logic circuitry for processing the sensed values and determining the control signals that are sent to the generator 20, rather than, or in combination with, the microprocessor 25.

The sensor module 22 may include a plurality of sensors (not explicitly shown) strategically located for sensing various properties or conditions, e.g., tissue impedance, voltage at the tissue site, current at the tissue site, etc. The sensors are provided with leads (or wireless) for transmitting information to the controller 24. The sensor module 22 may include control circuitry that receives information from multiple sensors, and provides the information and the source of the information (e.g., the particular sensor providing the information) to the controller 24.

More particularly, the sensor module 22 may include a real-time voltage sensing system (not explicitly shown) and a real-time current sensing system (not explicitly shown) for sensing real-time values related to applied voltage and current at the surgical site. Additionally, an RMS voltage sensing system (not explicitly shown) and an RMS current sensing system (not explicitly shown) may be included for sensing and deriving RMS values for applied voltage and current at the surgical site.

RF output stage may include a switched inductor system 200 (FIG. 3) that is also known as a switching regulator. A switching regulator is a circuit that uses a switch, an inductor and a diode to transfer energy from an input to an output. The basic components of the switching circuit can be arranged to form a step-down (buck), step-up (boost), or an inverter (flyback). Switching regulators offer three main advantages compared to a linear regulators. First, switching efficiency can be much better than linear. Second, because less energy is lost in the transfer, smaller components and less thermal management are required. Third, the energy stored by an inductor in a switching regulator can be transformed to output voltages that can be greater than the input (boost), negative (inverter), or can even be transferred through a transformer to provide electrical isolation with respect to the input.

Figure 3:
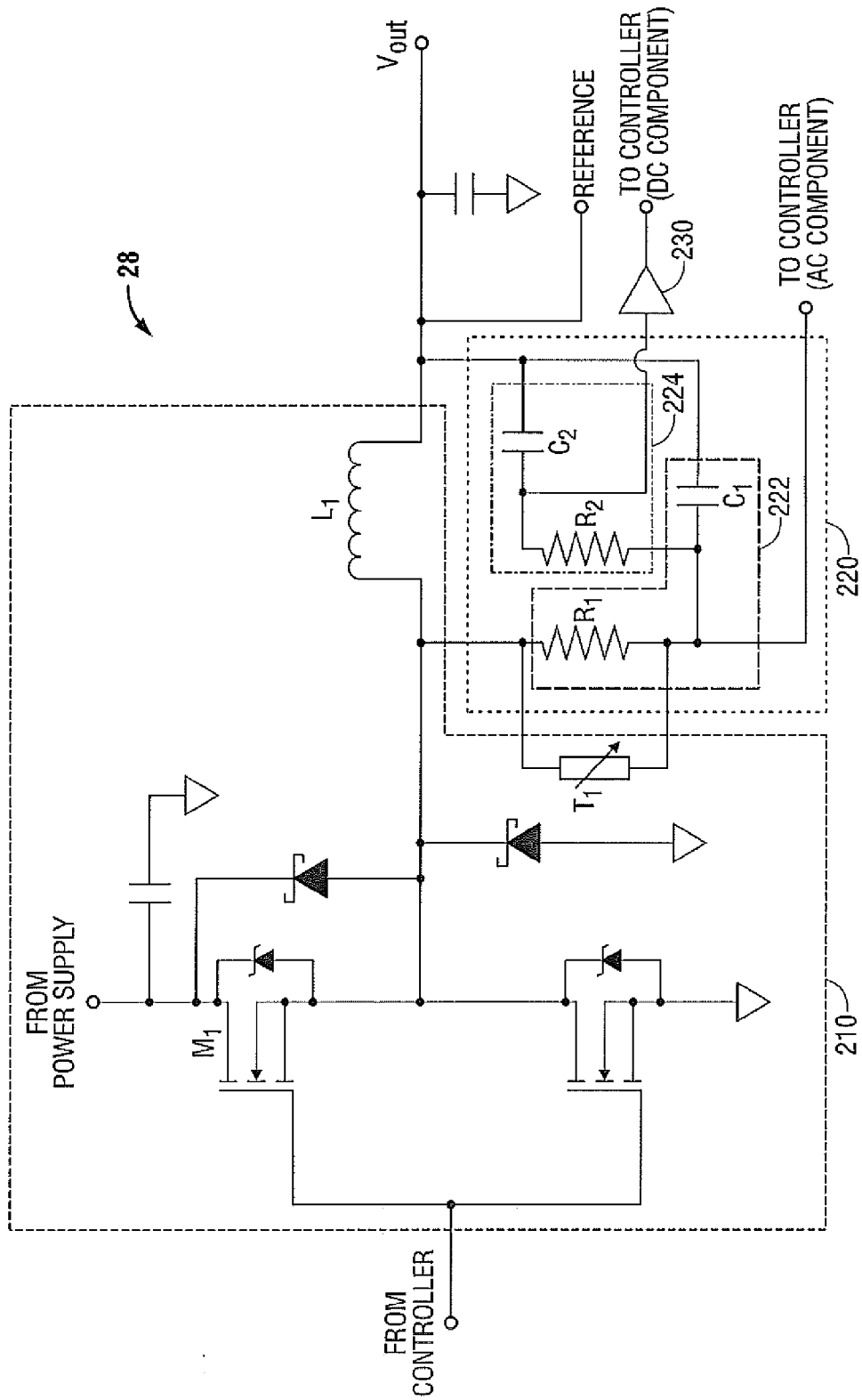
FIG. 3 is a schematic diagram of the power supply of FIG. 2 according to an embodiment of the present disclosure.

FIG. 3 is a schematic diagram of a switched inductor system 200 according to an embodiment of the present disclosure. As shown in FIG. 3, system 200 has a switching regulator 210 and a sensing circuit 220. Although FIG. 3 shows a switching regulator 210 having a step-down or buck type configuration, one skilled in the art may also use a step-up (boost) or inverter (flyback) configuration in conjunction with sensing circuit 220 by placing sensing circuit 220 in parallel with the inductor. System 200 is operatively coupled to and powered by power supply 27. System 200 is also operatively coupled to controller 24. Controller 24 provides a signal to control field effect transistors (FETs) M1 and M2 of switching regulator 210 to control the output of system 200. Switching regulator 210 also includes an inductor L1. Inductor L1 may be a one turn inductor which is less likely to fail than other inductors.

Sensing circuit 220 is operatively coupled in parallel with inductor L1. Sensing circuit 220 includes an RC network having a first RC circuit 222 with a resistor R1 in series with capacitor C1 and a second RC circuit 224 with resistor R2 in series with capacitor R2. Cycle by cycle and average power supply currents can be determined by sensing the voltage across the inherent series resistance of inductor L1 using the first RC circuit 222 composed of resistor R1 and capacitor C1. The voltage across inductor L1 is reproduced across capacitor C1. Because the voltage across inductor L1 is too small for accurate cycle by cycle detection, the values of resistor R1 and capacitor C1 are modified to amplify the alternating current (AC) component of the inductor's voltage. For example, the values of R1 and C1 may be modified to amplify the AC component by 100 at the capacitor.

Second RC circuit 224 may be used to restore the direct current (DC) component of the signal and may be connected across capacitor C1 or inductor L1. The voltage across C2 may be inputted into an amplifier 230 to match the amplification of the AC component. The amplified DC component may then be added to the AC component to restore the DC offset and provided to controller 24 to monitor system power. Alternatively, the DC component may be further modified to provide a measure of power supply output current by converting the DC component voltage to an appropriate level to be sent to controller 24 or another monitoring device.

During operation of the electrosurgical generator 20, inductor L1 may saturate or the temperature of inductor L1 may rise thereby leading to inaccurate readings if the voltage was measured across the inductor. By adding sensing circuit 220, more accurate measurements may be taken because the RC network of sensing circuit 220 does not see saturation or temperature rise. Further, because the RC network can measure the voltage drops across capacitors C1 and C2 cycle by cycle, more efficient control of the power output may be achieved thereby making the generator 20 more efficient and reducing the amount of heat generated by the generator 20.

Optionally, as shown in FIG. 3, a thermistor T1 may be provided in parallel with resistor R1 with thermal linkage to inductor L1 to monitor the temperature of inductor L1. Thermistor T1 may provide controller 24 with a signal indicative of the temperature of inductor L1 which may then control the output of power supply 27 or RF output stage 28 based on the temperature of inductor L1.

Although FIG. 3 depicts a particular circuit arrangement, modifications may be made to system 200 without departing from the disclosure. For instance, inductor L1, resistors R1 and R2 and capacitors C1 and C2 may each be replaced by one or more equivalent components. Also, inductor L1 may replaced with a variable inductor while resistors R1 and R2 may be replaced by one or more potentiometers and capacitors C1 and C2 may be replaced by variable capacitors.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A switched inductor system, comprising:
a switching regulator configured to receive an input signal and provide a voltage output, the switching regulator having at least one switch and at least one inductor; and
a sensing circuit in parallel with the inductor, the sensing circuit including a first RC circuit configured to detect an alternating current component of the voltage output and a second RC circuit configured to detect a direct current component of the voltage output.

2. The switched inductor system of claim 1, wherein the at least one switch is a field effect transistor.

3. The switched inductor system of claim 1, wherein the first RC circuit has at least one resistor and at least one capacitor.

4. The switched inductor system of claim 1, wherein the second RC circuit has at least one resistor and at least one capacitor.

5. An electrosurgical generator, comprising:
a controller configured to control a voltage output of the electrosurgical generator; and
a radio frequency output stage configure to output energy, the radio frequency output stage comprising:
a switching regulator configured to receive an input signal from the controller and provide a voltage output, the switching regulator having at least one switch and at least one inductor; and
a sensing circuit in parallel with the inductor, the sensing circuit including a first RC circuit configured to detect an alternating current component of the voltage output and a second RC circuit configured to detect a direct current component of the voltage output;
wherein the sensing circuit provides the alternating current component and the direct current component of the voltage output to the controller; and
wherein the controller controls the output of the electrosurgical generator based on the alternating current component and the direct current component of the voltage output.

6. The electrosurgical generator of claim 5, wherein the sensing circuit further includes an amplifier that amplifies the direct current component of the voltage output.

7. The switched inductor system of claim 5, wherein the at least one switch is a field effect transistor.

8. The switched inductor system of claim 5, wherein the first RC circuit has at least one resistor and at least one capacitor.

9. The switched inductor system of claim 5, wherein the second RC circuit has at least one resistor and at least one capacitor.

\* \* \* \* \*